United States Patent [19]
Pilgrimm

[11] Patent Number: 5,160,725
[45] Date of Patent: Nov. 3, 1992

[54] MAGNETIC LIQUID COMPOSITIONS

[75] Inventor: Herbert Pilgrimm, Berlin, Fed. Rep. of Germany

[73] Assignee: Silica Gel Gesellschaft mbH Adsorptions-Technik, Apparatebau, Berlin, Fed. Rep. of Germany

[21] Appl. No.: 638,134

[22] Filed: Jan. 4, 1991

Related U.S. Application Data

[63] Continuation-in-part of Ser. No. 173,590, Mar. 25, 1988, abandoned.

[30] Foreign Application Priority Data

Mar. 24, 1987 [DE] Fed. Rep. of Germany ....... 3709851

[51] Int. Cl.$^5$ ............................................ A61K 49/00
[52] U.S. Cl. ...................................................... 424/9
[58] Field of Search ............................................ 424/9

[56] References Cited

U.S. PATENT DOCUMENTS 4,267,234 4/1981 Rembaum ........................... 428/403
4,423,158 12/1983 Porath ..................................... 521/32
4,554,088 11/1985 Whitehead et al. .............. 252/62.54

FOREIGN PATENT DOCUMENTS 0125995 5/1984 European Pat. Off. .
186616A 11/1984 European Pat. Off. .

*Primary Examiner*—S. J. Friedman
*Assistant Examiner*—T. J. Criares
*Attorney, Agent, or Firm*—Anderson Kill Olick & Oshinsky

[57] ABSTRACT

Magnetic liquid compositions are prepared from physiologically tolerated dispersions of stabilized superparamegnetic particles in water or aqueous salt solution and reactive stabilizer substances chemically bonded over phosphate, phosphonate or carboxylate groups to the surface of the superparamagnetic particles. The reactive stabilizer substances stabilize and chemically bond diagnostic and pharmacologically active substances.

11 Claims, No Drawings

MAGNETIC LIQUID COMPOSITIONS

This is a continuation-in-part, of application Ser. No. 07/173,590, filed Mar. 25, 1988, now abandoned.

The invention relates to magnetic liquid compositions, which comprise physiologically tolerated dispersions of stabilized superparamagnetic particles in water and to an amount of reactive stabilizer substances, which is sufficient to stabilize and chemically bond diagnostic and pharmacologically active substances, the stabilizer substances being chemically bonded over phosphate, phosphonate or carboxylate groups to the surface of the superparamagnetic particles.

When used as a contrasting agent in image-forming diagnosis, they bring about an increase in the contrast of the image and in the selectivity, while at the same time they make it possible to reduce the concentration relative to that of conventional contrasting agents. Moreover, a plurality of new tissue-specific contrasting agents and new contrasting methods arise, as well various possibilities of use in medicine and veterinary medicine.

The increase in the contrast of the image can be achieved in nuclear spin tomography of, for example, paramagnetic ions, such as $Cr^{3+}$, $Mn^{2+}$, $Fe^{2+}$, $Fe^{3+}$, $Co^{2+}$, $Ni^{2+}$, $Cu^{2+}$, $Gd^{2+}$ or with stable free radicals.

Because the magnetic moments of these substances are low, their concentration must be relative high in order to achieve an effective improvement in contrast. Since most of the substances are relatively toxic at higher concentrations, the applicability of the ions can be improved only by complexing.

Increasing the magnetic moments of contrasting agents leads to the use of larger magnetic particles, as, for example, the German Patent Application 3,590,398, the U.S. Pat. Nos. 4,675,173 and 4,615,879 and WO 85/04330. Ferromagnetic microparticles are proposed here with Weiss regions of the order of a few hundred Angstroms up to about 1 $\mu$m. These microparticles are provided with a polymer coating, to which substances with bonding affinity for tissue are coupled.

Ferromagnetic microparticles of the proposed size have such large magnetic moments, that the particles associate to larger aggregates, even when they are provided with a polymer coating. Already during the coating process are the particles present as aggregates. Such ferromagnetic microparticles would settle in the body after parenteral administration, without reaching the specific bonding site. The residence time of large ferromagnetic microparticles and of their aggregates in the body is long and the danger of toxic side effects is great.

The dispersions of ferromagnetic particles used in German Patent Applications 3,443,251 and 3,443,252 have similar disadvantages. The magnetic interactions between the particles here lead to aggregation and sedimentation.

The magnetic particles are coated with monosaccharides, oligosaccharides, polysaccharides, proteins or synthetic protective colloids, these substances being bonded to the magnetic particles by way of adsorptive interaction. All factors, which affect the structure and composition of the molecular layer of stabilizer, may have destabilizing effects, that is, the magnetic particles may aggregate and settle. The proposed stabilizer substances provide only weakly stabilized magnetic particles, some of which settle immediately or on storage. An accumulation of the magnetic particles in the organism is therefore nonspecific, while the danger of toxic side effects is large. Sedimentation of the magnetic particles takes place very rapidly, especially under the influence of magnetic fields. If magnetic field inhomogeneities occur, the magnetic particles will always concentrate at the sites of highest field strength. These disadvantages arise especially in NMR diagnostic methods with high magnetic field strengths.

In WO 85/02772, magnetic particles are stabilized with molecules, which are not bonded covalently. Such adsorption-stabilized magnetic particles are not stable under physiological conditions, since the magnetic particles readily aggregate due to detachment of the stabilizer substances. If substances with bonding affinity for certain tissues are coupled to adsorption-stabilized magnetic particles, the danger exists that the stabilizer substances and thus the substances with bonding affinity are detached from the contrast-producing magnetic particles and the latter do not reach the site of bonding.

The previously prepared, physiologically tolerated, aqueous magnetic liquids have been produced by adsorption of stabilizer substances. The dextran magnetites of U.S. Pat. No. 4,101,435 and the albumin magnetites of U.S. Pat. No. 4,452,773 are also stabilized by adsorption of larger macromolecules, which have a diameter similar to that of the magnetic particles, so that the effective magnetic field of the magnetic particles on neighboring tissue is greatly reduced compared to stabilization with small molecules. With these magnetic liquids also, competitive adsorption and destabilization, which can lead to aggregation of the magnetic particles, occur on dilution with blood. The magnetic particles do not reach the desired bonding site, if tissue-specific bonding substances are coupled.

It is an object of the invention, which is defined in claim 1, to produce new magnetic liquid compositions, in order to avoid the disadvantages cited above and to open up new areas of application. Pursuant to the invention, this objective is accomplished owing to the fact that very small superparamagnetic single-domain particles are used, which are protected against aggregation by chemically bonding reactive stabilizer substances to their surface.

The superparamagnetic particles have a magnetic moment, which is substantially higher than that of paramagnetic ions, radicals or oxygen, and which reaches approximately the maximum value, which is theoretically possible for the particular material composition.

The magnetic particles therefore are very effective in reducing the relaxation times of adjacent atomic nuclei and molecules, which are capable of resonating, so that the effective concentration can be reduced by several orders of magnitude relative to that of the paramagnetic substances.

It is advantageous to produce the superparamagnetic particles as small as possible, so as to keep the biological half-life time and the toxicity as low as possible and to be able to produce stable magnetic liquids from these particles, which can be sterilized by filtration or the action of heat and do not aggregate in very strong magnetic fields.

Pursuant to the invention, very small superparamagnetic particles can be prepared by precipitation with alkaline solutions from saturated, iron solutions containing organic solvents. Surprisingly, it was discovered that almost monodisperse superparamagnetic particles can be produced very simply by adding to an iron solution a water-miscible, such as acetone, ethyl methyl ketone or dioxane, until the incipient opacity is barely dissolved once again by stirring. The superparamagnetic particles can be precipitated from such a solution, for example, with sodium hydroxide solution. The concentration of the iron salt solution determines the size of the particles formed; the size varies inversely with the concentration of the iron salt solution.

The diameters of the magnetic particles ranges from 1 to 20 nm and preferably from 3 to 10 nm. Due to their large specific surface area (approx. 100 m$^2$/g), they dissolve very rapidly, that is, their biological half-life time is very short (1-3 days).

As physiologically tolerated magnetic materials, such products as $\alpha$-Fe$_2$O$_3$, $\gamma$-Fe$_2$O$_3$ or Fe$_3$O$_4$ are used. Elements such as fluorine or phosphorus may be contained in physiologically safe amounts in the particles. By these means, the diagnosis can also be extended to fluorine or phosphorus NMR diagnosis and the contrast in radiological diagnosis can be increased by incorporating iodine.

Pursuant to the invention, the magnetic particles are stabilized by chemically bonding stabilizer substances to their surface. The stabilizer substances must have at least one chemically reactive functional groups, such as a carboxyl, phosphate or phosphonate group, by means of which they are bonded chemically to the surface of the magnetic particles.

The remainder of the molecule must be such, that it is miscible with the dispersants used and keeps the distance between the magnetic particles sufficiently large, so that the kinetic energy of the magnetic particles is greater than the magnetic interaction energy.

Surprisingly, it was found that the chemical bonds formed by organic, water-soluble mono-, di- or triphosphate esters, mono-, di- or triphosphoric acid chloride esters and mono- and diphosphates or phosphonates with the surface of the magnetic particles, are very resistant to hydrolysis. Water soluble carboxylic acids form stable magnetic liquids only at an elevated temperature and in anhydrous solvents, for example, by azeotropic distillation of the water formed during the reaction.

These magnetic liquid compositions are however not stable against hydrolysis. However, it has surprisingly been found that water-soluble magnetic liquid compositions are formed which are stable against aggregation and hydrolysis, provided polycarboxylic acids are used as stabilizer substance. Without wanting to be limited by any theories, it is assumed that the plurality of the polycarboxylic acid bonds which enter a stabilizer molecule with the oxide-hydrate surface of the magnetic particles is responsible for the stability.

Moreover, it has surprisingly been found that polyethyleneglycol containing carboxylic acid may successfully be used as stabilizer substance. It is assumed that the polyethyleneglycol chains orient themselves through hydrogen bridge linkages in such a manner "polycarboxylic acid-like" structures are formed which cause the aggregation and hydrolysis stability.

For the aqueous, magnetic liquid compositions, the magnetic substances may comprise, for example, polyethyleneglycol derivatives, such as mono- and di-polyethyleneglycol phosphate, phosphonate or carboxylic acid, or mono- and di-polypropyleneglycol/polyethyleneglycol phosphate, phosphonate or carboxylic acid, the number of propylene glycol and ethylene glycol groups being between 2 and 100, $\omega$-alkoxy-polyethyleneglycol and $\omega$-alkoxy-propyleneglycol/polyethyleneglycol phosphate, phosphonate or carboxylic acid, the number of carbon atoms of the alkyl groups between 1 and 5, phosphoric acid-containing biomolecules, such a mono-, di- or triphosphate esters or mono, di- or triphosphoric acid chlorides of adenosine, guanosine, cytidine, uridine, thymidine, desoxyadenosine, desoxyguanosine, desoxycytidine, desoxythymidine, inosine, pyrimidine, cytosine, uracil, thymine, purine, adenine, guanine, methylcytosine, 5-hydroxymethylcytosine, 2-methyladenine, 1-methylguanine, thiamine, flavine, riboflavine, as well as pyridoxal phosphate, pyridoxamine phosphate, ribonucleic acids, desoxyribonucleic acids, ribonucleic acid sequences, desoxyribonucleic acid sequences, orotidylic acid, carboxylic acid-containing biomolecules, such as biotin, biocytin, folic acid, tetrahydrofolic acid, N$^5$, N$^{10}$-methyltetrahydrofolic acid, $\alpha$-liponic acid, dihydroliponic acid, phosphoric acid- and/or carboxylic acid-containing carbohydrates, the carbohydrates comprising monosaccharides, such as glucose, fructose, ribose, desoxyribose, inositol, oligosaccharides, such as sucrose, raffinose, gentianose, malecitose, stachyose, verbascose, polysaccharides, such as starch, lichenins, glycogen, dextrins, dextrans, inulins, fructosans, levans, mannans, galactans, xylans, arabans, pectins, macropolysaccharides, glycoproteids, polyuridylic acid, polyglucuronic acid, polygalcturonic acid, polymannuronic acid, alginic acid, or linear functionalized synthetic polymers, such as polymethacrylic acid or polyacrylic acid.

For fat-soluble magnetic liquid compositions, the stabilizer substances comprise, for example, carboxyl group-containing biomolecules, such as oleic acid, linoleic acid, linolenic acid, cholic acid or glycocholic acid.

Pursuant to the invention, several stabilizer substances can be bonded chemically to the surface of the magnetic particles (DE 3,709,852), by which means the dispersing properties can be varied within wide limits. For example, strongly polar substances, such as polyethyleneglycol phosphate and weakly polar stabilizer substances, such as oleic acid, can be bonded to the surface of the magnetic particles, so that such particles can be transported in aqueous blood and accumulated in fat-containing tissue.

The chemical stabilization of the magnetic particles makes it possible to prepare magnetic liquid compositions, which cannot be prepared with known, adsorption-stabilized magnetic liquids, because in competitive adsorption the more strongly adsorbed substance displaces the less strongly adsorbed one.

The magnetic particles, stabilized chemically in this manner, do not settle even under the action of strong magnetic fields. This is very important when they are used in NMR diagnosis. Upon parenteral administration, the stabilizer substances are not stripped off, as they are with the known adsorption-stabilized magnetic particles; in other words, there is no aggregation and no sedimentation in the blood. The particles are therefore dispersed well in the organism. Only when the chemically bonded stabilizer substances are broken down can aggregation of the magnetic particles take place.

Pursuant to the invention, tissue-specific bonding substances can be coupled to the stabilizer substances bound to the surface of the magnetic particles, provided that the stabilizers still have free, chemically reactive groups, such as hydroxyl, amine, aldehyde, epoxy, thiol, carboxyl, 4,6-trichlorotriazine, hydroxamic acid, isocyanate, acylazide, anhydride, diazonium salt or iminocarbonate groups.

Such stabilizers are, for example, oligo- or polysaccharide phosphates or carboxylic acids, which are provided with the appropriate functional groups before or after they are bonded to the magnetic particles. The functionalization techniques are known from the immobilization methods of biochemistry and from the state of the art. Aside from these reactive stabilizing substances based on carbohydrates, functionalized polyethyleneglycols, polypropyleneglycols or polyethyleneglycol/polypropyleneglycols, such as ω-oxoalkoxypolyethyleneglycol phosphate, phosphonate or carboxylic acid or their acetals, ω-aminoalkoxy-polyethyleneglycol phosphate, phosphonate or carboxylic acid, ω-oxoalkylamino-polyethyleneglycol phosphate, phosphonate or carboxylic acid or their acetals, ω-oxoalkoxy-propyleneglycol phosphate, phosphonate or carboxylic acid or their acetals, ω-oxoalkoxy-polyethyleneglycol/polypropyleneglycol phosphate, phosphonate or carboxylic acid or their acetals, ω-oxoalkylamino-polyethyleneglycol/polypropyleneglycol phosphate, phosphonate or carboxylic acid or their acetals, or reactive phosphorus-containing biomolecules, such as pyridoxal phosphate, pyridoxamine phosphate or cocarboxylase are usable as reactive stabilizers.

Pursuant to the invention, the tissue-specific bonding substances, such as antigens, antibodies, haptens, ribonucleic acids, desoxyribonucleic acids, protein A, hormones or hormone analogs, can be coupled to the reactive stabilizer substances, which are bonded to the surface of the magnetic particles.

The tissue-specific bonding substances, so bonded chemically by way of the stabilizer substances to the magnetic particles, form liquids, which are stable in magnetic fields, do not agglomerate and therefore are dispersed well in the body and accumulate at the bonding sides. There is also no desorption of the stabilizer or bonding substances in the body fluid. Only when the substances are broken down enzymatically are the magnetic particles destabilized.

Aside from tissue-specific bonding substances, pharmacologically active substances, such as antitumor proteins, antitumor enzymes, antibiotics, plant alkaloids, alkylating reagents, lymphokines, tissue plasminogen activators, urokinase lymphotoxins, macrophage activating bodies, tumor necrosis factors, can also be coupled pursuant to the invention to the free, reactive groups of the stabilizer substances, so that, aside from the tissue-specific accumulations of magnetic particles, a pharmacological effect can also be achieved at the bonding site.

The toxicity of such pharmacologically active substances may, at the same time, be relatively high, since the magnetic particles, because of their tissue specific interaction, accumulate preferentially at the appropriate bonding sites, where they exert their pharmacological effect, such as controlling tumors. The dose of pharmacologically active substance can be kept low, because the substance is concentrated at the site of action and the rest of the body is affected but little.

For some substances, for example, the tissue plasminogen activators, urokinase, the tissue-specific bonding properties and the pharmacological action properties are coupled, so that only these substances need to be bonded to the stabilizer substances in order to bring about a specific accumulation at the blood clot and its dissolution.

The coupling of pharmacological active substances to magnetic particles furthermore has the advantage that the success of the therapy can be observed by a shortening of the relaxation time at the site of action using in vivo NMR diagnostic means.

Pursuant to the invention, pharmacologically effective biologically active particles, such as organelles, viruses, microbes, algae, fungi, cells and here especially erythrocytes, leukocytes, thrombocytes and Langerhans' islets can be coupled to the reactive stabilizers, which are bonded to the surface of the magnetic particles.

These biological particles, which are surrounded by a layer of magnetic particles a few nm thick, can be used as NMR and ultrasonic contrasting agents.

A further area of application of these biologically active magnetic particles is the production of physiological important metabolic products in the body or the removal of toxic materials from the body by fixing the magnetic, biologically active particles in the circulating blood or in body cavities by magnetic, high-gradient fields. For example, magnetic Langerhans' islets can be fixed in body cavities by strong inhomogeneous magnetic fields and used for the production of insulin in the case of diabetes.

Pursuant to the invention, pharmacologically active complexing agents, such as polycarboxylic acids, aminocarboxylic acids, porphyrins or catecholamines, can be bound to the reactive stabilizer substances, which are bonded to the surface of the magnetic particles. Such magnetic liquid compositions can be used to bind toxic substances in the body, which form a compound with the magnetic complexing agents. The magnetic complexes formed can be removed with the help of high-gradient magnetic fields.

For example, the circulating blood can be passed through a hose assembly outside of the body and a magnetic liquid composition can be added continuously to the circulating blood. This magnetic liquid composition magnetizes the toxic components or other components of the blood, such as viruses, bacteria or cancer cells and removes them from the blood in a high-gradient magnetic field.

Pursuant to the invention, iodine-containing reactive substances, such as 2,4,6-triiodobenzoic acid, 2,4,6-triiodoisophthalic acid, 2,4,6-triiodo-5-aminoisophthalic acid, 2,4,6-triiodophenylacetic acid, 2,4,6-triiodophenylpropionic acid and their derivatives, 3,5-diiodotyrosine and L-thyroxin, can be bonded chemically to the reactive stabilizer substances, which are bonded to the surface of the magnetic particles.

Compared to previous iodine-containing contrasting agents, the radiological contrasting agents, so formed, have improved properties, since the local volume concentration of the absorptive iron and iodine atoms is very high, less of the contrasting agents is required and the magnetic contrasting agents are tolerated better and do not diffuse into the extracellular space.

Pursuant to the invention, a combination of positive contrast-forming paramagnetic metal complexes or free nitroxide radicals and negative contrast-forming magnetic liquid compositions can be used to increase the contrast in NMR diagnosis. The individual contrasting agents can be administered consecutively or simultaneously in the form of mixtures. The paramagnetic metal complexes, which diffuse into the extracellular space, furnish a positive NMR contrast in the vascular wall and the magnetic liquid compositions, which do not diffuse through the vascular wall, furnish a negative NMR contrast.

Pursuant to the inventio, NMR-active elements, such as phosphorus and fluorine, may be contained in the magnetic particles and in the stabilizer substances so that, aside from the proton resonance, the phosphorus and fluorine resonances and the changes in relaxation times caused by these elements become usable for NMR diagnosis.

For example, in the preparation of superparamagnetic particles by precipitation, fluorine and/or phosphorus atoms, in the form of, for example, fluoride, phosphate or hexafluorophosphate ions, may be introduced into the magnetic particles. The magnetic particles will then supply fluorine and/or phosphorus NMR signals, which can be utilized for diagnostic purposes.

Similar effect can also be attained by chemically bonding fluorine and/or phosphorus-containing substances, in addition to the above-named stabilizer substances, to the surface of the magnetic particles. Such stabilizer substances are, for example, perfluoroalkoxypolyethyleneglycol phosphate, carboxylic acids, phosphonates, sulfonamide phosphates, or sulfonamide phosphonates, perfluoroalkylcarboxylic acids, phosphates, phosphonates, sulfonamide phosphates, sulfonamide phosphonates or sulfonamide carboxylic acids, perfluoropolyethyleneglycol phosphate or phosphonate, phytic acid or carbohydrates containing phosphoric acid and/or carboxylic acid groups, which have flourine-containing substituents, such as perfluoroalkyl, perfluoroalkoxypolyethyleneglycol and perfluoroaklylsulfonamide groups.

Pursuant to the invention, iodine-containing radiological contrasting agents, which contain phosphate, phosphonate or carboxyl groups, can be bonded chemically to the surface of the magnetic particles in addition to the above-named stabilizer substances, so that radiological contrasting agents with a high absorptive capacity for X-radiation result. As already stated above, such iodine-containing contrasting agents are, for example, 2,4,6-triiodobenzoic acid and its derivatives.

The magnetic liquid composition is prepared by mixing the superparamagnetic particles with the stabilizing substances and the dispersant and subsequently reacting the reactive functional groups of the stabilizer substances thermally and/or catalytically with the hydroxyl groups on the surface of the magnetic particles.

The superparamagnetic particles can be prepared by mechanically comminuting larger magnetic particles, by thermally decomposing iron carbonyls and then selectively reacting with steam or by precipitating iron salts and appropriately oxidizing or reducing the precipitates.

The preparation pursuant to the invention of magnetite powders is to be explained using an example.

EXAMPLE 1

Iron (III) chloride (270 g) and 99 g of iron (II) chloride are dissolved in 500 mL of water. By addition of acetone up to incipient cloudiness, the iron salt solution is converted into a saturated iron salt solution. The pH is brought to a value of 10.5 by addition of sodium hydroxide or ammonium hydroxide and the mixture is heated to 70° C. After cooling, the precipitate formed is filtered or centrifuged off and washed with water until free of chloride. The magnetite particles formed can either be processed further immediately or dried gently at a low temperature under vacuum.

By passing in a mixture of air and steam for 2 hours at 100° C., superparamagnetic $\alpha$-$Fe_2O_3$ can be prepared from these magnetite particles.

If the magnetite particles are heated in an autoclave in an air-steam atmosphere to 250° C., the superparamagnetic $\gamma$-$Fe_2O_3$ particles are formed.

The magnetic particles are stabilized at different temperatures depending on the reactivity of the stabilizer molecules. Since the reactions involved are condensation reactions, the water formed must be removed, for example, in the case of fat-soluble liquids by, for example, azeotropic distillation.

EXAMPLE 2

$\alpha$-$Fe_2O_3$ powder (10 g) is mixed with 2.5 g of linolenic acid and 200 mL of naphtha and refluxed with stirring in an apparatus with water separator. At the end of the water separation, the magnetic liquid formed is filtered and the dispersion is concentrated to dryness. The residue is soluble in paraffin oil and produces a liquid, which is stable in magnetic fields and suitable for NMR diagnosis.

EXAMPLE 3

Magnetite powder (10 g) is mixed with 3 g of $\omega$-methoxy-decaethyleneglycol phosphate and 100 mL of water and stirred for 2 hours in an autoclave at 140° C. The sterile, aqueous, magnetic liquid formed is filtered through a 0.2 $\mu$m filter and the excess stabilization substance is removed by dialysis. The magnetic liquid formed is mixed with sodium chloride to form a 0.9% salt dispersion. After dilution with physiological salt solution to the desired final concentration, the NMR diagnostic magnetic liquid composition can be bottled and heat sterilized.

When stabilizing the magnetic particles with two or more stabilizer substances, attention must be paid to the desired stochiometric ratio which determines the dispersion properties of the resulting stabilized magnetic particles. For example, a $\gamma$-$Fe_2O_3$ powder, which is mixed with 3 parts of pentaethyleneglycol phosphate and 1 part of oleic acid, is not readily miscible with water or naphtha. However, a material, such as n-butyl acetate, is a suitable dispersant.

EXAMPLE 4

$\gamma$-$Fe_2O_3$ (10 g) is mixed with 2.3 g of methoxy-decaethyleneglycol carboxylic acid, 0.8 g of oleic acid and 100 mL of n-butyl acetate and refluxed for 4 hours in an apparatus with water separator. The stable magnetic liquid formed is filtered and the n-butyl acetate is evaporated under vacuum. A residue is formed, which is soluble in physiological salt solution and can be used as a liquid composition for NMR diagnosis.

EXAMPLE 5

Carbonyl iron powder (10 g), which has a hydrated oxide layer on the surface due to a steam treatment, is mixed with 4 g of polyuridylic acid, 100 mL of methyl isobutyl ketone and 0.5 g of p-toluenesulfonic acid as catalyst and refluxed for 12 hours in an apparatus with water separator. The stable magnetic liquid formed is filtered and the methyl isobutyl ketone is evaporated under vacuum. The residue is dispersed in water and the resulting magnetic liquid is freed from excess stabilizer substance by dialysis. Sodium chloride is added to the dialysate up to a physiological salt concentration. The product represents an effective magnetic liquid composition for NMR diagnosis.

The stabilization of magnetic particles with stabilizer substances, which are suitable for bonding tissue-specific or pharmacologically which are suitable for bonding tissue-specific or pharmacologically active substances, can be accomplished as described in Example 3. The subsequent coupling of the tissue-specific bonding substances and of the pharmacologically active substances is carried out according to the state of the art, depending on the available reactive groups.

EXAMPLE 6

Magnetite powder (10 g) of Example 1 is mixed with 3.5 g of polygalacturonic acid and 100 mL of water and stirred for 2 hours in an autoclave at 140° C. The magnetic liquid formed is filtered through a 0.2 μm filter and dialyzed against water. To 10 mL of this magnetic liquid (20 mg of stabilized magnetite/mL of magnetic liquid), 10 mM of sodium periodate are added. After a 2-hour oxidation, the mixture is dialyzed against a cold 0.02M sodium borate buffer solution having a pH of 8.5. The magnetite particles formed have aldehyde groups on the chemically bonded polygalacturonic acid molecules. These aldehyde groups can be caused to react, for example, with amino groups of tissue-specific bonding substances and/or pharmacologically active substances. The Schiff's bases, formed by these reactions, are subsequently stabilized with sodium borohydride.

EXAMPLE 7

Magnetic liquid (1 mL), which has been oxidized with potassium periodate as in Example 6, is stirred with 1 mL of human γ-globulin (1 mg/mL) and, after 12 hours, reduced for 60 minutes by the addition of 1 mL of 0.2M sodium borohydride solution. The resulting magnetic liquid is dialyzed against physiological salt solution and contains chemically bonded γ-globulin on magnetic particles stabilized with polygalacturonic acid. This magnetic liquid composition is suitable for NMR diagnosis.

EXAMPLE 8

Magnetite powder (10 g) of Example 1 is mixed with 4 g of ω-oxoalkylamino-polyethyleneglycol phosphate, having 20 ethylene glycol units, in 20 mL of water and dispersed for 30 minutes in an ultrasonic bath at 80° C. The resulting reactive magnetic liquid is mixed with 2 g of 2,4,6-triiodo-5-aminoisophthalic acid and dialyzed after 20 minutes against a physiological salt solution. After filtration through a 0.2 μm filter, the resulting magnetic liquid composition is usable as a radiological contrasting agent.

EXAMPLE 9

Magnetite powder (10 g) of Example 1 is mixed with 4 g of ω-oxoalkoxy-decapolyethyleneglycol phosphonate and with 20 mL of physiological salt solution and dispersed for 30 minutes in an ultrasonic bath at 80° C. The resulting reactive magnetic liquid is mixed with 5 g of erythrocytes and allowed to stand for 30 minutes at room temperature. The resulting magnetic liquid composition is mixed with 4 g of urea and, after 10 minutes, dialyzed against physiological salt solution.

In in vivo applications, the magnetic liquid compositions of the invention are stored largely in the liver and broken down there, so that magnetic liquid compositions with cytostatic activity, which contain, for example, ω-oxoalkoxypolyethyleneglycol phosphate, phosphonate or carboxylic acid or ω-oxoalkylaminopolyethyleneglycol phosphate, phosphonate or carboxylic acid or their acetals as stabilizers, can be used for the treatment of liver tumors even without tissue-specific bonding substances.

The resulting magnetic liquid compositions can be used for ultrasonic diagnosis.

Magnetic particles with phosphorus and fluorine atoms can easily be produced by precipitating iron oxide in the presence of hexafluorophosphoric acid.

EXAMPLE 10

Iron (III) chloride (270 g) and iron (II) chloride (99 g) are dissolved in 500 mL of water and treated with 75% hexafluorophosphoric acid (10 g). The pH is adjusted to 10.5 by the addition of ammonia water and the mixture is heated to 70° C. After cooling, the precipitate is filtered or centrifuged off and washed with water until free of chloride. The fluorine content of the magnetic particles is 5% by weight.

EXAMPLE 11

The magnetite powder (10 g) of Example 10 is mixed with 8 g of aminoethoxypolyethylene glycol phosphate (with a molecular weight of about 1,000) and 30 mL of water and dispersed for 30 minutes in the ultrasonic bath. The dispersion is dialyzed against distilled water and filtered through a 0.2 μm filter.

This magnetic liquid composition is suitable for NMR diagnosis and can also be used for the coupling of organic compounds, for example, for the coupling of fluorine-containing organic compounds.

EXAMPLE 12

To 10 mL of the magnetic liquid of example 11, 1 g of perfluorooctanoic acid and 1 g of 1-cyclohexyl-3-(2-morpholinoethyl) carbodiimide metho-p-toluene-sulfonate (Merck) are added and dispersed for 30 minutes at room temperature in the ultrasonic bath. The dispersion is dialyzed against a physiological salt solution and filtered through a 0.2 μm filter. This magnetic liquid composition is suitable for fluorine NMR diagnosis.

Magnetic liquid compositions with different adsorption properties can be prepared by using stabilizer substances with different proportions of ethylene glycol and propylene glycol.

EXAMPLE 13

Polyethylene glycol/polypropylene glycol (Pluronic 85 ® from Fluka) with approximately 75 ethylene glycol units and 55 propylene glycol units is heated to 50° C. mixed with 0.4 g of pyrophosphoric acid and stirred for 24 hours with exclusion of moisture. The resulting phosphate is dissolved in 30 mL of distilled water, treated with 10 g of magnetite powder as in Example 1 and dispersed for 30 minutes at 60° C. in the ultrasonic bath. The dispersion is dialyzed against physiological salt solution and filtered through a 0.2 μm filter. This magnetic liquid composition is suitable for NMR diagnosis.

Magnetic liquid compositions with iodine-containing organic compounds, which find application in X-ray diagnosis as well as in NMR diagnosis, can be synthesized, for example, from polyethylene glycol phosphates having aldehyde groups and iodine compounds having amino groups.

EXAMPLE 14

—$Fe_2O_3$ powder (10 g) is mixed with 10 g of ω-oxoethoxypolyethylene glycol phosphate dimethylacetal (with a molecular weight of about 2,000) and 30 mL of distilled water and dispersed for 30 mL of distilled water and dispersed for 30 minutes at 70° C. in the ultrasonic bath. The dispersion is dialyzed against distilled water and filtered through a 0.2 μm filter. To the dispersion, 1 mL of 1N hydrochloric acid is added and the mixture is incubated for 1 hour at room temperature. The pH is then adjusted to 6.5 by the addition of 1N sodium hydroxide solution. To this dispersion 3 g of 2,4,6-triiodo-5-aminoisophthalic acid are added and stirred for 30 minutes at room temperature. The resulting dispersion is subsequently incubated overnight at room temperature with 1.5 mL of a 0.5% sodium borohydride solution. The dispersion is dialyzed against physiological salt solution and filtered through a 0.2 μm filter. This magnetic liquid composition is suitable for NMR and X-ray diagnoses.

Reactive magnetic liquids can also be prepared from mixtures of materials. In this case, one of the components acts as stabilizer to prevent aggregation of the magnetic particles in the magnetic field and the second component acts as reactant for coupling binding substances.

EXAMPLE 15

Magnetite powder (10 g) of Example 1 is suspended in 30 mL of distilled water, mixed with 6 g of ethoxypolyethylene glycol phosphate (with a molecular weight of about 1,000) and 0.5 g of pyridoxal-5-phosphate and dispersed for 60 minutes at 40° C. in the ultrasonic bath. The dispersion is dialyzed against distilled water and filtered through a 0.2 μm filter.

This magnetic liquid composition is suitable for coupling binding substances containing amino groups.

EXAMPLE 16

The magnetic liquid of example 15 (10 mL) is mixed with 10 mL of 0.01M borate-HCl buffer (pH of 8.1), 5 mL of a 1 mg/mL solution of streptokinase (Boeringer, Mannheim) in physiological salt solution and 1.5 mL of a 0.5% aqueous sodium cyanoborohydride solutions and incubated overnight at +4° C. To block the remaining aldehyde groups of the pyridoxal-5-phosphate, 3 mL of a 0.5 molar ethanolamine hydrochloride solution (pH 8.5) and 0.6 mL of a 2.5% sodium borohydride solution are added, incubated 1 hour at +4° C. and dialyzed against physiological salt solution. After filtration through a 0.2 μm filter, a magnetic liquid composition results, which finds application in NMR diagnosis and for the treatment of thromboses. The liquid must be stored at +4° C.

Further examples of the preparation of magnetic liquid compositions for NMR diagnosis are:

EXAMPLE 17

The magnetite powder of Example 1 (10 g) is mixed with 7 g of polyethylene glycol dicarboxylic acid (with a molecular weight of about 1,500) in 30 mL of water and dispersed for 60 minutes at 60° C. in the ultrasonic bath. The dispersion is dialyzed against physiological salt solution and filtered through a 0.2 μm filter. This magnetic liquid composition is suitable for NMR diagnosis.

EXAMPLE 18

Magnetite powder of Example 1 (10 g) is mixed with 10 g of ω-methoxypolyethylene glycol phosphate (with a molecular weight of about 1,000) in 30 mL of distilled water and dispersed for 30 minutes at 80° C. in the ultrasonic bath. The resulting magnetic liquid is dialyzed against water and filtered through a 0.2 μm filter. To this solution, 45 g of mannitol and 0.04 g of methyl 4-hydroxybenzoate are added and the dispersion is lyophilized.

The resulting black powder can be stored for several years and, when needed, dissolved in distilled water and used for enteral NMR diagnosis. For gastrointestinal applications, this magnetic liquid composition has the advantage that it can pass through the gastrointestinal tract without noticeably aggregating or dissolving. The dosage should be about 40 μg of iron per kg of body weight and, in comparison to other contrasting agents, is very low. The contrasting agent is not absorbed by the intestines.

EXAMPLE 19

The magnetite powder of Example 1 (10 g) is mixed with 6 g of thiamine monophosphate chloride in 30 mL of water and dispersed for 60 minutes at 40° C. in the ultrasonic hath. The dispersion is dialyzed against physiological salt solution and filtered through a 0.2 μm filter. This magnetic liquid composition is suitable for NMR diagnosis.

EXAMPLE 20

Dextran (10 g, molecular weight of about 6,000) is suspended in 100 mL of methylene chloride, mixed with 0.3 g of pyrophosphoric acid and refluxed for 10 hours. To this suspension, 30 mL of distilled water are added and the methylene chloride is distilled off. To this dextran phosphate solution, 10 g of the magnetite powder of Example 1 are added and is dispersed for 30 minutes at 70° C. in the ultrasonic bath. The dispersion is dialyzed against physiological salt solution and filtered through a 0.2 μm filter. The resulting magnetic liquid composition is suitable for NMR diagnosis.

This dextran phosphate, which is chemically bound to the magnetite, is superior to the previously known dextran magnetites, since the dextran molecules cannot be detached from the surface of the magnetite particle. This is of importance in the case of the chemical coupling of organic binding substances and biological particles.

EXAMPLE 21

To 10 mL of the magnetic liquid of Example 20, 25 mL of a 40% by weight sodium hydroxide solution are added and 15 g of chloroacetic acid are added dropwise with stirring. After 30 minutes, 1.5 g of sodium hydroxide are added and the whole is stirred for 2 hours. The solution is subsequently neutralized with 50% acetic acid, dialyzed against distilled water and filtered through a 0.2 μm filter. The degree of substitution is 0.9%. The carboxymethyl group-containing magnetic liquid formed can be used for the coupling of binding substances and of biological particles.

EXAMPLE 22

To 10 mL of the magnetic liquid of Example 21, 40 mL of a 0.01M boratehydrochloric acid buffer (pH of 8.1) and 0.5 mL of an antihuman Ig 61 solution (from the Sigma company) are added with stirring. After that, 1 g of 1-cyclohexyl-3-(2-morpholinoethyl) carbodiimide metho-p-toluenesulfonate (from the Merck company) is added and stirred for 24 hours at +4° C. The dispersion is dialyzed against physiological salt solution and filtered through a 0.2 μm filter. The magnetic liquid composition can be used for NMR diagnosis or for in vitro diagnosis.

In analogy to Example 22, other binding substances or also biological particles can also be bound.

For purposes of parenteral NMR diagnostics, magnetic liquid compositions with iron concentrations in the range of 10 to 40 μg/kg body weight, have been found to be particularly suitable. As compared to the presently known NMR diagnostic agents on the basis of paramagnetic salt solutions, the concentration of the contrast agent can be lowered by several orders of magnitude. The body load of the examined patient is also lowered in this manner.

For purposes of gastrointestinal NRM diagnosis, iron concentrations of 20 to 60 μg/kg body weight are found to be advantageous. These contrast agents pass through the stomach/intestine region without noticeable aggregation or without being chemically decomposed. Moreover, these contrast agents are not resorbed by the intestine. i.e., the contrast agent is harmless to the organism.

The magnetic liquid compositions of the invention can be used for nuclear spin tomography, as well as for local nuclear magnetic resonance spectroscopy. When fluorine-containing magnetic liquid compositions are used, there is the possibility of easy identification in the body, since the average concentration of the fluorine atom in the body is very low.

Aside from this important in vivo application, the magnetic liquid compositions can also be used for in vitro diagnosis, for example, as a magnetic DNA probe. For this purpose, DNA sequences, which are specific for a particular pathogenic DNA, are isolated and bonded to magnetic particles. These DNA sequence-containing magnetic liquids are now added to clinical samples, in which the viral or bacterial DNA was exposed as single strands. Hybridization takes place if the sample contains the pathogenic DNA in question. The sample can now be examined by NMR spectroscopy or the hybridization products can be isolated, washed and analyzed in the high-gradient magnetic field.

Employing this principle, the magnetic liquid composition with tissue-specific bonding substances can be used for in vitro diagnosis in various applications.

The magnetic liquid compositions of the invention, especially if stabilized with polyethyleneglycol phosphate or ethoxy-polyethyleneglycol phosphate, are broken down in the body to iron, which largely reappears as erythrocytes formed by the body. They may therefore be used as iron preparations in iron deficiency diseases.

The magnetic liquid compositions of the invention can also be used as magnetic carriers for the transport of pharmacologically active substances, the accumulation of magnetic particles in certain tissue and body areas being supported by the action of inhomogeneous magnetic fields.

The magnetic liquid compositions of the invention may also be used variously in technology, for example, for the separation of solids of different density in the magnetic field, to magnetize bacteria, viruses, cells, etc., in biotechnology and in biological effluent purification, as an absorption liquid in magnetic methods of separating materials and as an absorption liquid for radiation from the sun.

I claim:

1. A magnetic liquid composition, comprising:
   (a) a dispersion of superparamagnetic iron oxide and iron particles dispersed in an amount of from 0.1% to 50% by weight in water or aqueous salt solution, and in an amount of from 10% to 100% by weight of at least one of
   (b) reactive aggregation preventing organic substances of ω-alkoxy-polyethyleneglycols containing phosphate and phosphonate, polyethylene glycol/polypropyleneglycol containing phosphate and phosphonate, phosphoric acid-containing nucleotides, their oligomers or polymers, carbohydrates containing phosphoric acid groups, which have one chemically reactive phosphate and phosphonate group for the chemical bonding to the surface of the superparamagnetic particles, and
   (c) reactive aggregation preventing organic substances of polyethylene glycols, ω-aminoalkoxy-polyethyleneglycols, ω-oxoalkoxy-polyethyleneglycols containing phosphate and phosphonate, phosphoric acid-containing nucleotides, their oligomers or polymers, carbohydrates containing phosphoric acid groups, which have two chemically reactive functional groups, one of the functional groups being phosphate or phosphonate for the chemical bonding to the surface of the superparamagnetic particles and the other reactive functional group serving to couple covalently organic molecules.

2. The magnetic liquid composition of claim 1, wherein the superparamagnetic particles are selected from the group consisting of α-Fe$_2$O$_3$, γ-Fe$_2$O$_3$, Fe$_3$O$_4$ and iron and the particle diameter is between 3 and 10 nm.

3. The magnetic liquid composition of claim 1, wherein the particles are of iron oxide and the iron oxide particles contain up to 10% by weight of at least one of phosphorous and fluorine and the particle diameter is between 3 and 10 nm.

4. The magnetic liquid composition of claim 1, wherein the reactive aggregation preventing organic substances (b) are ω-alkoxy-polyethyleneglycol phosphate and phosphonate and the number of carbon atoms of the alkoxy groups is between 1 and 4 and the number of ethylene glycol groups is between 3 and 100.

5. The magnetic liquid composition of claim 1, wherein the reactive organic substances (b) have one chemically reactive phosphate and phosphonate group for chemical bonding to the surface of the superparamagnetic particles, and wherein the reactive organic substances are selected from the group consisting of polyethyleneglycol mono- and di-phosphate and phosphonate, the number of ethyleneglycol groups being between 3 and 100;

polyethyleneglycol/polypropyleneglycol mono- and di-phosphate and phosphonate, the number of propyleneglycol groups being between 2 and 100 and the number of ethyleneglycol groups being between 2 and 100;

the phosphoric acid-containing biomolecules mono-, di- and triphosphate esters and mono-, di- and triphosphoric acid chlorides of adenosine, guanosine, cytidine, uridine, thymidine, desoxyadenosine, desoxyguanosine, desoxycytidine, desoxythymidine, inosine, pyrimidine, cytosine, uracil, thymine, purine, adenine, guanine, methylcytosine, 5-hydroxymethylcytosine, 2-methyladenine, 1-methylguanine, thiamine, flavine, riboflavine, and pyridoxal phosphate, pyridoxamine phosphate, ribonucleic acids, desoxyribonucleic acids, ribonucleic acid sequences, desoxyribonucleic acid sequences, orotidylic acid;

phosphoric acid containing carbohydrates, the carbohydrate groups comprising the monosaccharides, glucose, fructose, ribose, desoxyribose, inositol;

the oligosaccharides, sucrose, raffinose, gentianose, malecitose, stachyose, verbascose;

the polysaccharides, starch, lichenins, glycogen, dextrins, dextrans, inulins, fructosans, levans, mannans, galactans, xylans, arabans, pectins, macropolysaccharides, glycoproteids.

6. The magnetic liquid composition of claim 1, wherein the organic substances (c) have at least two chemically reactive functional groups, one of the functional groups being phosphate or phosphonate for chemical bonding to the superparamagnetic particles and the other reactive functional group serving to bond organic molecules, and wherein the reactive organic substances comprise at least one member selected from the group consisting of ω-oxoalkoxy-polyethyleneglycol phosphate and phosphonate and their acetals, ω-oxoalkylamino-polyethyleneglycol phosphate and phosphonate and their acetals, ω-aminoalkoxy-polyethyleneglycol phosphate and phosphonate, ω-aminoalkylaminopolyethyleneglycol phosphate and phosphonate, the number of carbon atoms of the alkyl groups being between 1 and 5 and the number of ethyleneglycol groups between 2 and 100;

the phosphoric acid group containing carbohydrates comprising reactive functional groups selected from the group consisting of aldehyde, amine, oxirane, 4,6-dichlortriazine, isocyanate, acylazide, anhydride, diazonium salt and iminocarbonate groups.

7. The magnetic liquid composition of claim 6, wherein said functional groups are selected from the group consisting of hydroxyl, amine, aldehyde, oxirane, thiole, 4,6-dichlortriazine, hydroxamic acid, isocyanate, acylazide, anhydride, diazonium salt and iminocarbonate groups.

8. The magnetic liquid composition of claim 1, wherein the composition, in addition to said reactive organic substance (b), comprises at least one fluorine-containing reactive substance (d) which is chemically linked to the surface of the superparamagnetic particles, said substance (d) being selected from the group consisting of perfluoroalkyl phosphates, phosphonates, sulfonamide phosphates and sulfonamide phosphonates, ω-perfluoroalkoxypolyethyleneglycol phosphates and phosphonates, perfluoroalkylcaraboxylic acids; ω-perfluoroalkoxy-polyethyleneglycol carboxylic acids, perfluoroalkylsulfonamide carboxylic acids, perfluoropolyethyleneglycol phosphates and phosphonates, and the number of carbon atoms of the perfluoroalkyl groups being between 2 and 8 and the number of polyethylene glycol groups being between 4 and 100;

iodine-containing reactive substances, 2,4,6-triiodobenzoic acid, 2,4,6-triiodo-isophthalic acid, 2,4,6-triiodo-5-aminoisophthalic acid, 2,4,6-triiodophenylacetic acid, 2,4,6-triiodo-phenylpropionic acid and their derivatives, 3,5-diiodo-tyrosine and L-thyroxine.

9. The magnetic liquid composition of claim 3, wherein the composition, in addition to said reactive organic substances (b), comprises at least one fluorine-containing reactive substance (d) which is chemically linked to the surface of the superparamagnetic particles, said substance (d) being selected from the group consisting of perfluoroalkyl phosphates, phosphonates, sulfonamide phosphates and sulfonamide phosphonate, ω-perfluoroalkoxypolyethyleneglycol phosphates and phosphonates, perfluoroalkylcarboxylic acids; ω-perfluoroalkoxy-polyethyleneglycol carboxylic acids, perfluoroalkylsulfonamide carboxylic acids, perfluoropolyethyleneglycol phosphates and phosphonates, and the number of carbon atoms of the perfluoroalkyl groups being between 2 and 8 and the number of polyethylene glycol groups being between 4 and 100;

iodine-containing reactive substances, 2,4,6-triiodobenzoic acid, 2,4,6-triiodo-isophthalic acid, 2,4,6-triiodo-5-aminoisophthalic acid, 2,4,6-triiodophenylacetic acid, 2,4,6-triiodo-phenylpropionic acid and their derivatives, 3,5-diiodo-tyrosine and L-thyroxine.

10. The magnetic liquid composition of claim 6, wherein the composition, in addition to said reactive organic substance (c), comprises at least one fluorine-containing reactive substance (d) which is chemically linked to the surface of the superparamagnetic particles, said substance (d) being selected from the group consisting of perfluoroalkyl phosphates, phosphonates, sulfonamide phosphates and sulfonamide phosphonate, ω-perfluoroalkoxy-polyethyleneglycol phosphates and phosphonates, perfluoroalkylcarboxylic acids;

ω-perfluoroalkoxy-polyethyleneglycol carboxylic acids, perfluoroalkylsulfonamide carboxylic acids, perfluoropolyethyleneglycol phosphates and phosphonates, and the number of carbon atoms of the perfluoroalkyl groups being between 2 and 8 and the number of polyethylene glycol groups being between 4 and 100;

iodine-containing reactive substances, 2,4,6-triiodobenzoic acid, 2,4,6-triiodo-isophthalic acid, 2,4,6-triiodo-5-aminoisophthalic acid, 2,4,6-triiodophenylacetic acid, 2,4,6-triiodo-phenylpropionic acid and their derivatives, 3,5-diiodo-tyrosine and L-thyroxine.

11. The magnetic liquid composition of claim 6, wherein tissue-specific bonding substances selected from the group consisting of antigens, antibodies, ribonucleic acids, desoxyribonucleic acids, ribonucleic acid sequences, desoxyribonucleic acid sequences, haptens, protein A, hormones, hormone analogs, antitumor proteins, enzymes, antitumor enzymes, plant alkaloids, alkylating reagents, lymphokines, lymphotoxins, urokinse, tissue plasminogen activators, macrophage activators, tumor necrosis factors;

particles, selected from the group consisting of viruses, microbes, algae, fungi, cells, erythrocytes, leukocytes, Langerhans' islets;

complexing agents, selected from the group consisting of polycarboxylic acids, aminocarboxylic acids, porphyrins, catecholamines, fluorine-containing and iodine-containing reactive substances are chemically bonded to the reactive organic substances (c), which are chemically bonded to the surface of the superparamagnetic particles.

* * * * *